US012344589B2

(12) United States Patent
Kiguchi et al.

(10) Patent No.: US 12,344,589 B2
(45) Date of Patent: Jul. 1, 2025

(54) METHOD FOR PRODUCING A 1,5-BENZOTHIAZEPIN COMPOUND

(71) Applicant: Elobix AB, Gothenburg (SE)

(72) Inventors: Shinya Kiguchi, Izumo (JP); Ganapati G. Bhat, Bangalore (IN); Johnson M. Coutinho, Bangalore (IN); Mikael Dahlstrom, Mölndal (SE); Michael Lofthagen, Stockholm (SE); Akinori Tatara, Kanagawa (JP)

(73) Assignee: ELOBIX AB, Gothenburg (SE)

( * ) Notice: Subject to any disclaimer, the term of this patent is extended or adjusted under 35 U.S.C. 154(b) by 518 days.

(21) Appl. No.: 17/639,296

(22) PCT Filed: Aug. 27, 2020

(86) PCT No.: PCT/JP2020/032378
§ 371 (c)(1),
(2) Date: Feb. 28, 2022

(87) PCT Pub. No.: WO2021/049311
PCT Pub. Date: Mar. 18, 2021

(65) Prior Publication Data
US 2022/0315547 A1    Oct. 6, 2022

(30) Foreign Application Priority Data
Sep. 9, 2019 (IN) .............................. 201911036177
Nov. 13, 2019 (JP) ................................ 2019-205580

(51) Int. Cl.
*C07D 281/10* (2006.01)
*A61K 31/554* (2006.01)

(52) U.S. Cl.
CPC .................................. *C07D 281/10* (2013.01)

(58) Field of Classification Search
CPC ................ C07D 281/10; A61K 31/554; C07K 5/06026
See application file for complete search history.

(56) References Cited

U.S. PATENT DOCUMENTS

| 7,192,946 | B2 | 3/2007 | Starke et al. |
| 10,428,109 | B1 | 10/2019 | Bhat et al. |
| 10,995,115 | B2 | 5/2021 | Bhat et al. |
| 2017/0143738 | A1 | 5/2017 | Ando et al. |
| 2017/0143783 | A1 | 5/2017 | Ando et al. |
| 2020/0109165 | A1 | 4/2020 | Bhat et al. |

FOREIGN PATENT DOCUMENTS

| JP | 2004516285 | 6/2004 |
| JP | 2004521961 | 7/2004 |
| JP | 2016522181 | 7/2016 |
| JP | 2017537061 | 12/2017 |
| WO | WO 200166533 | 9/2001 |
| WO | WO 200250051 | 6/2002 |
| WO | WO 2003020710 | 3/2003 |
| WO | WO 2003022286 | 3/2003 |
| WO | WO 2003022825 | 3/2003 |
| WO | WO 2003091232 | 11/2003 |
| WO | WO 2003106482 | 12/2003 |
| WO | WO 2004089350 | 10/2004 |
| WO | WO 2012064266 | 5/2012 |
| WO | WO 2014174066 | 10/2014 |
| WO | WO 2016062848 | 4/2016 |

OTHER PUBLICATIONS

Dunetz et al., "Large-Scale Applications of Amide Coupling Reagents for the Synthesis of Pharmaceuticals," Organic Process Research & Development, 2016, 20(2):140-177.
Kunishima et al., "Synthesis and Application Development for Novel Triazine Dehydration Concentration Agent," Wako Pure Medicine Times, Nov. 2003, 72(2):8-11.
PCT International Preliminary Report on Patentability in International Application No. PCT/JP2020/032378, dated Mar. 9, 2022, 9 pages (with English translation).
PCT International Search Report and Written Opinion in Application No. PCT/SE2019/050208, dated Jul. 8, 2019, 15 pages.
PCT International Search Report and Written Opinion in International Application No. PCT/JP2020/032378, dated Oct. 20, 2020, 19 pages (with English translation).
SE Search Report in Swedish Application No. 1850474-6, dated Oct. 11, 2018, 3 pages.

*Primary Examiner* — Brenda L Coleman
(74) *Attorney, Agent, or Firm* — Fish & Richardson P.C.

(57) ABSTRACT

The present invention relates to a process for the preparation of a compound of formula (I) comprising: reacting a compound of formula (II) with a compound of formula (III) in the presence of a triazine compound to obtain a compound of formula (IV), and deprotecting said compound of formula (IV) to obtain the compound of formula (I). The compound of formula (I) can be prepared by the process according to the present invention in high yields and high purity. In addition, the process according to the present invention does not use a large amount of solvents or require a purification process of intermediate compounds.

23 Claims, No Drawings

METHOD FOR PRODUCING A 1,5-BENZOTHIAZEPIN COMPOUND

CROSS-REFERENCE TO RELATED APPLICATIONS

This application is a National Stage application under 35 U.S.C. § 371 of International Application No. PCT/JP2020/032378, having an International Filing Date of Aug. 27, 2020, which claims priority to Indian Application No. 201911036177, filed on Sep. 9, 2019, and to Japanese Application Serial No. 2019-205580, filed on Nov. 13, 2019. The disclosures of the prior applications are considered part of the disclosure of this application, and are incorporated in their entireties into this application.

TECHNICAL FIELD

The present invention relates to a process for the preparation of 1,5-benzothiazepine compounds.

BACKGROUND ART

N-{(2R)-2-[({[3,3-dibutyl-7-(methylthio)-1,1-dioxido-5-phenyl-2,3,4,5-tetrahydro-1,5-benzothiazepin-8-yl]oxy}acetyl)amino]-2-phenylethanolyl}glycine (elobixibat) is an ileal bile acid transporter (IBAT) inhibitor and can be used in the treatment of prevention of dyslipidemia, constipation, diabetes and liver diseases.

The processes for the preparation of 1,5-benzothiazepine compounds including elobixibat is disclosed in WO 02/50051, for example. Specifically, the compounds can be prepared by oxidizing benzothiazepine followed by removing a protecting group thereof. However, the process disclosed in WO 02/50051 requires a large number of steps, and uses several reagents.

On the other hand, the process using many reagents is not desirable from an environmental and safety perspective. For example, if different solvents depending on steps are used in the process, it is necessary to remove the solvents when the steps are completed. Therefore, a multiple solvents are required in a large amount, and the cost for removing the solvents are expensive. In addition, a further step of purification of the obtained product in each step is also necessary, and thus the process is not suitable for an industrial scale production.

WO 2014/174066 discloses a process for the preparation of a crystalline monohydrate of elobixibat. However, the process disclosed in WO 2014/174066 is not suitable for an industrial scale production.

Thus, there is a need for an improved process for the preparation of 1,5-benzothiazepine compounds, which is suitable for an industrial scale production. In particular, an improved process in which 1,5-benzothiazepine compounds in higher yields and higher purity than previous processes can be obtained at low cost for the preparation.

SUMMARY OF INVENTION

The present invention is conducted in order to solve the problem in the prior arts. The purpose of the present invention is to provide a process for the preparation of 1,5-benzothiazepine compounds in high yields and high purity with a reduce amount of solvents without repeating purification steps of intermediate compounds.

As a result of a careful study by the inventors of the present invention, a process in which 1,5-benzothiazepine compounds can be obtained in high yields and high purity using one kind of solvent in multiple steps by using triazine compound, was unexpectedly found.

The purpose of the present invention can be achieved by a process for the preparation of a compound of formula (I):

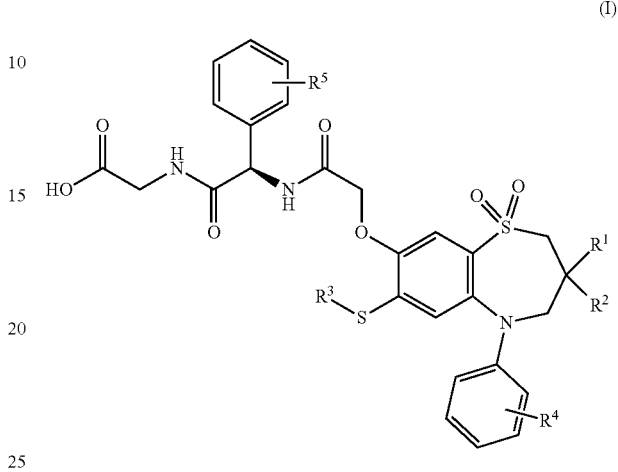

(I)

wherein
$R^1$ and $R^2$ are each independently $C_{1-4}$ alkyl;
$R^3$ is $C_{1-4}$ alkyl;
$R^4$ is selected from the group consisting of hydrogen, hydroxy, halo, nitro, cyano and $C_{1-4}$ alkyl; and
$R^5$ is selected from the group consisting of hydrogen, hydroxy, halo, nitro, cyano and $C_{1-4}$ alkyl;
comprising reacting a compound of formula (II)

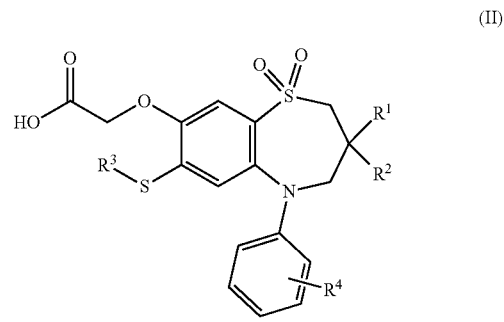

(II)

wherein $R^1$ to $R^4$ are as defined above,
with a compound of formula (III) in the presence of a triazine compound:

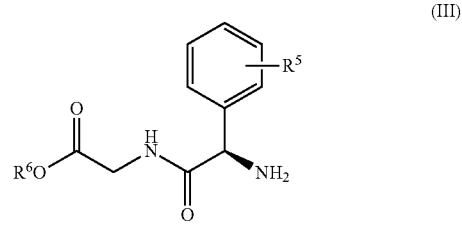

(III)

wherein
$R^5$ is as defined above; and
$R^6$ is a protecting group;

to obtain a compound of formula (IV):

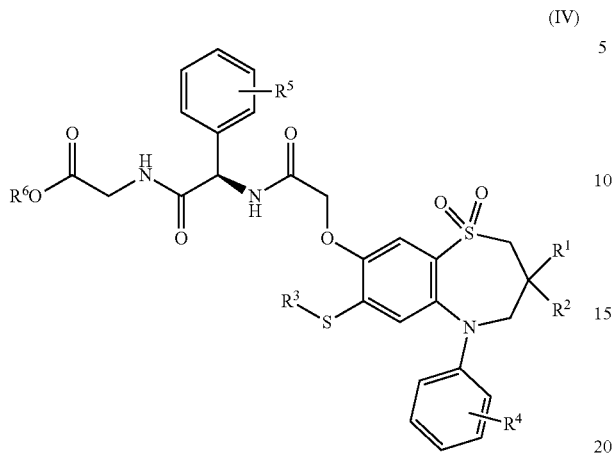

wherein $R^1$ to $R^6$ are as defined above,
and deprotecting said compound of formula (IV) to obtain the compound of formula (I).

It is preferable that the triazine compound is selected from the group consisting of 2,4,6-trichloro-1,3,5-triazine (TCT), 2-chloro-4,6-dimethoxy-1,3,5-triazine (CDMT), 2,4-dichloro-6-methoxy-1,3,5-triazine (DCMT), 4-(4,6-dimethoxy-1,3,5-triazin-2-yl)-4-methylmorpholinium chloride (DMT-MM), and a mixture thereof. More preferably, the triazine compound is 4-(4,6-dimethoxy-1,3,5-triazin-2-yl)-4-methylmorpholinium chloride (DMT-MM).

It is preferable that $R^1$ and $R^2$ are each n-butyl in formulae (I), (II), and (IV).

It is preferable that $R^3$ is methyl in formulae (I), (II), and (IV).

It is preferable that $R^4$ and $R^5$ are each hydrogen in formulae (I), (II), (III), and (IV).

It is preferable that $R^6$ is selected from the group consisting of $C_{1-4}$ alkyl and trisubstituted silyl in formulae (III) and (IV). It is more preferable that $R^6$ is tert-butyl.

It is preferable that the compound of formula (IV) is deprotected by reacting with trifluoroacetic acid.

It is preferable that the step of deprotecting said compound of formula (IV) is performed in the presence of toluene and water, and the amount of water used is 0.2 to 2.0% by weight with respect to the amount of toluene.

It is preferable that the compound of formula (I) is precipitated from a solution by the addition of heptane.

It is preferable that the compound of formula (II) is prepared by an alkylation reaction comprising reacting a compound of formula (V):

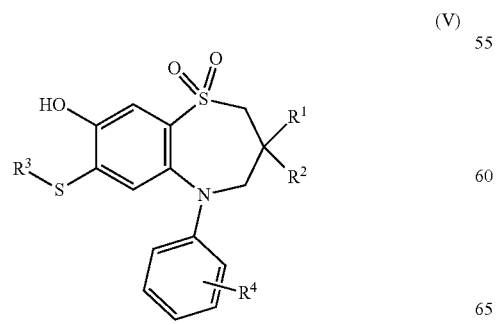

wherein $R^1$ to $R^4$ are as defined above,
with a compound of formula (VI) in the presence of water:

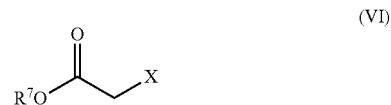

wherein
$R^7$ is a protecting group; and
X is a leaving group;
to obtain an intermediate compound of formula (VII):

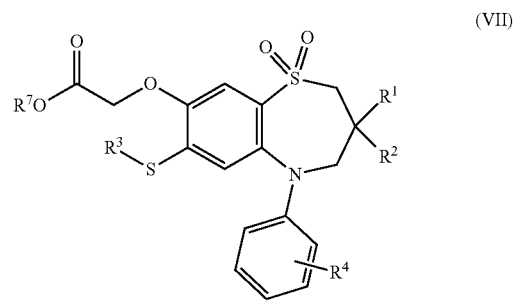

wherein $R^1$ to $R^4$ and $R^7$ are as defined above,
followed by hydrolysis of the ester $R^7O$—C(O)—,
to obtain the compound of formula (II).

It is preferable that $R^7$ is selected from the group consisting of $C_{1-4}$ alkyl and $C_{1-4}$ haloalkyl in formulae (VI) and (VII).

It is preferable that X is selected from the group consisting of halo, trifluoromethanesulfonate, methanesulfonyl and p-toluenesulfonyl.

It is preferable that the preparation of the intermediate compound of formula (VII) is performed in toluene.

It is preferable that the amount of water used in the reaction of the compound of formula (V) with the compound of formula (VI) is 0.01 to 0.5% by weight with respect to the amount of the compound of formula (V).

It is preferable that the intermediate compound of formula (VII) is not isolated and used directly in the next step.

It is preferable that the alkylation reaction and the subsequent hydrolysis reaction are performed in the same solvent.

It is preferable that the compound of formula (III) is prepared by deprotecting a compound of formula (VIII) in the presence of a solvent of alcohol having 3 or more carbon atoms:

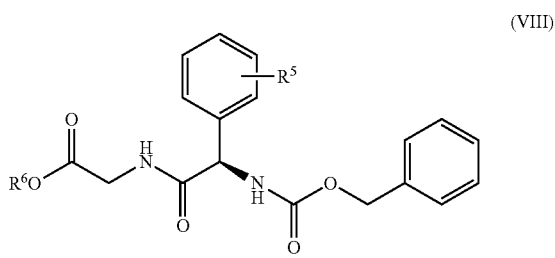

wherein $R^5$ and $R^6$ are as defined above.

It is preferable that the alcohol having 3 or more carbon atoms is selected from the group consisting of 1-propanol, 2-propanol, 1-butanol, 2-butanol, 2-methyl-1-propanol, 2-methyl-2-propanol, and a mixture thereof.

The process according to the present invention may further comprise transforming the compound of formula (I) into a stable crystalline hydrate of formula (I).

It is preferable that the compound of formula (I) is dissolved in ethyl acetate.

It is preferable that n-heptane is added to the solution of the compound of formula (I) in ethyl acetate.

It is preferable that the stable crystalline hydrate is a crystalline monohydrate.

By the present invention, 1,5-benzothiazepine compounds can be prepared in high yields and high purity by reacting the compound of formula (II) with the compound (III) in the presence of the triazine compound.

1,5-benzothiazepine compounds can be prepared without using a large amount of solvents in the environmental friendly process according to the present invention. In addition, the process according to the present invention does not require a purification process of intermediate compounds. Accordingly, the cost for the process is not expensive, and the process is suitable for an industrial scale production.

DETAILED DESCRIPTION OF INVENTION

The present invention relates to a process for the preparation of a compound of formula (I):

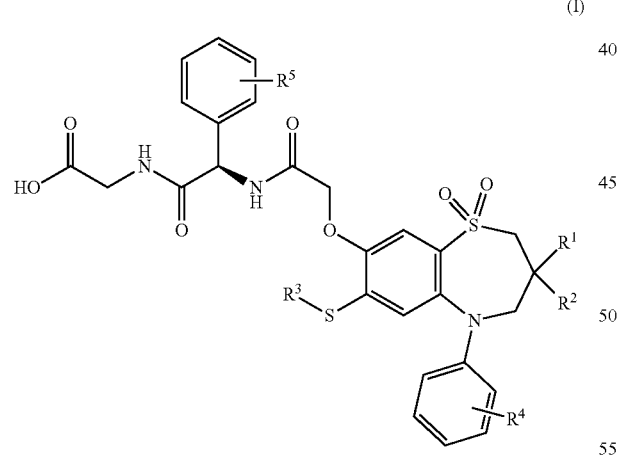

wherein
$R^1$ and $R^2$ are each independently $C_{1-4}$ alkyl;
$R^3$ is $C_{1-4}$ alkyl;
$R^4$ is selected from the group consisting of hydrogen, hydroxy, halo, nitro, cyano and $C_{1-4}$ alkyl; and
$R^5$ is selected from the group consisting of hydrogen, hydroxy, halo, nitro, cyano and $C_{1-4}$ alkyl;

comprising reacting a compound of formula (II)

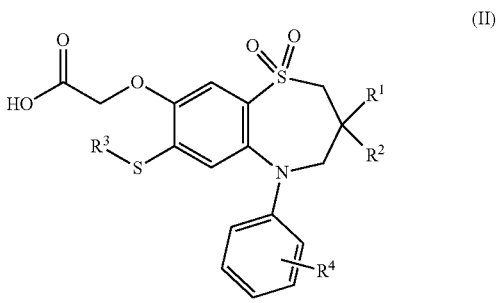

wherein $R^1$ to $R^4$ are as defined above,
with a compound of formula (III) in the presence of a triazine compound:

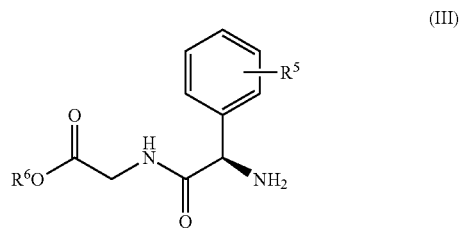

wherein
$R^5$ is as defined above; and
$R^6$ is a protecting group;
to obtain a compound of formula (IV):

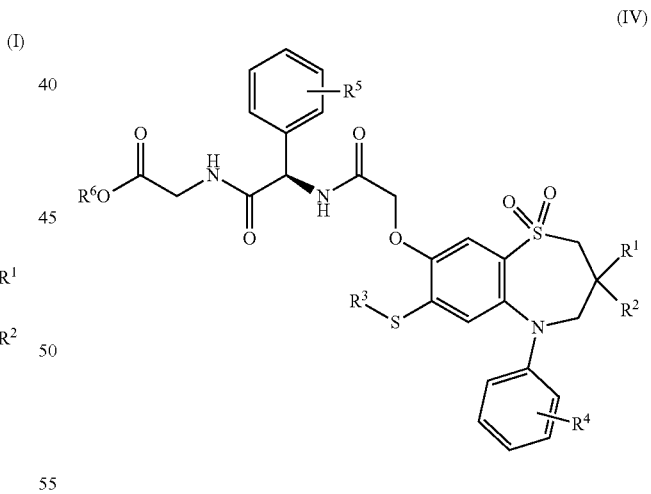

wherein $R^1$ to $R^6$ are as defined above,
and deprotecting said compound of formula (IV) to obtain the compound of formula (I).

As used herein, the term "alkyl" refers to both of a straight and branched alkyl groups. In addition, the term "halo" refers to fluoro, chloro, bromo and iodo.

As used herein, the term "$C_{1-4}$ alkyl" refers to a straight or branched alkyl group having from 1 to 4 carbon atoms. Examples of $C_{1-4}$ alkyl include methyl, ethyl, n-propyl, isopropyl, n-butyl, isobutyl, sec-butyl and tert-butyl.

As used herein, the term "$C_{1-4}$ haloalkyl" refers to a $C_{1-4}$ alkyl group as defined above, wherein at least one of the hydrogen atoms has been replaced with halogen. Examples of $C_{1-4}$ haloalkyl include fluoromethyl, difluoromethyl, and trifluoromethyl.

As used herein, the term "protecting group" refers to a temporary substituent which protects a potentially reactive functional group from undesired chemical transformations. Such protecting groups are well-known for a person skilled in the art, and described in T. W. Greene, Protective Groups in Organic Synthesis, John Wiley & Sons, 1999, for example. Specifically, esters of carboxylic acids, such as alkyl esters and silyl esters of carboxylic acids are exemplified.

In addition, in the process for the preparation of the compound of formula (I), the deprotecting can be performed by removing the protection group by any known technologies.

The compound of formula (I) can have a chiral center and/or a geometric center of an isomer. The compound of formula (I) of the present invention includes all optical and geometric isomers having IBAT inhibitory activity.

Furthermore, the compound of formula (I) may be in the form of pharmaceutically acceptable salts. When the compound of the present invention is basic, it may be an inorganic acid or organic acid salt thereof, for example, an acid-addition salt thereof with hydrochloric, hydrobromic, sulphuric, phosphoric, trifluoroacetic, citric, acetic or maleic acid. Also, when the compound of the present invention is acidic, it may be an alkali metal salt thereof such as a sodium or potassium salt, an alkali earth metal salt such as a calcium or magnesium salt, an ammonium salt, or a salt with an organic base which is capable of providing a physiologically acceptable cation such as methylamine, dimethylamine, trimethylamine, piperidine, morpholine, or tris(2-hydroxyethyl)amine.

The compound of formula (I) may be in the form of a prodrug which is capable of providing the compound of formula (I) by degrading in human or animal body. As examples of the prodrug, esters hydrolysable in vivo or amides hydrolysable in vitro of the compound of formula (I) are included.

Also, the compound of formula (I) may be a solvate such as a hydrate. The compound of formula (I) includes all solvates having IBAT inhibitory activity. In particular, the compound of formula (I) is preferably a crystalline hydrate, and more preferably a crystalline monohydrate.

In one embodiment, at least one of $R^1$ and $R^2$ in the compound of formula (I) is preferably n-butyl. More preferably, $R^1$ and $R^2$ are each n-butyl.

In one embodiment, $R^3$ in the compound of formula (I) is preferably methyl or ethyl. More preferably, $R^3$ is methyl.

In one embodiment, at least one of $R^4$ and $R^5$ in the compound of formula (I) is preferably hydrogen. More preferably, $R^4$ and $R^5$ are each hydrogen.

The process according to the present invention includes a step of reacting the compound of formula (II) with a compound of formula (III) in the presence of the triazine compound.

The compound of formula (III) is preferably used in excess of the compound of formula (II). The compound of formula (III) is used preferably in an amount of 1.0 to 1.3 equivalents and more preferably in an amount of 1.2 equivalents with respect to the compound of formula (II).

$R^6$ in the compound of formula (III) is a protecting group, preferably a protecting group that may be removed under acidic conditions. In one embodiment, $R^6$ is preferably selected from the group consisting of $C_{1-4}$ alkyl and trisubstituted silyl, more preferably is tert-butyl or trimethylsilyl, and most preferably is tert-butyl.

Preferably, the triazine compound is selected from the group consisting of 2,4,6-trichloro-1,3,5-triazine (TCT), 2-chloro-4,6-dimethoxy-1,3,5-triazine (CDMT), 2,4-dichloro-6-methoxy-1,3,5-triazine (DCMT), 4-(4,6-dimethoxy-1,3,5-triazin-2-yl)-4-methylmorpholinium chloride (DMT-MM), and a mixture thereof. The most preferred triazine compound is 4-(4,6-dimethoxy-1,3,5-triazin-2-yl)-4-methylmorpholinium chloride (DMT-MM). By using the triazine compounds, the same solvent as the solvent used in the step of producing the compound of formula (III) can be used, and thus the amount of solvent used can be reduced.

The triazine compound is preferably used in excess of the compound of formula (II). The triazine compound is preferably used in an amount of 1.0 to 1.5 equivalents with respect to the compound of formula (II).

The solvent used in not particularly limited, however, from the perspective of the amount of solvent used, it is preferred that the same solvent as the solvent used in the step of producing the compound of formula (III) is used.

The reaction of the compound of formula (II) with the compound of formula (III) in the presence of the triazine compound may be performed at a temperature between 0° C. and the boiling point of the solvent. The reaction is preferably performed at a temperature of 5° C. to 80° C., more preferably at a temperature of 10° C. to 40° C.

Once the reaction is completed, insoluble substances are removed by filtration, and can be washed by the same solvent as the solvent used in the reaction. Then, the filtrate may be condensed, and ethyl acetate may be added to the filtrate. The filtrate may be consecutively washed with water, an aqueous solution of acid (e.g., a 3% aqueous solution of hydrochloric acid), an aqueous solution of base (e.g., a 5% aqueous solution of sodium hydrogen carbonate), and saline. The product may be crystallized and filtrated, and then dried under vacuum to obtain the compound of formula (IV).

The process according to the present invention includes a step of deprotecting the compound of formula (IV) to obtain the compound of formula (I). The deprotecting is performed by hydrolysis of $C(O)OR^6$ group, and preferably by acid hydrolysis of the group. The hydrolysis can be performed in the presence of a suitable acid and results in the corresponding carboxylic acid of formula (I).

Examples of suitable acids include, but are not limited to, hydrochloric acid, sulfuric acid, nitric acid, methanesulfonic acid, p-toluenesulfonic acid, camphorsulfonic acid, benzenesulfonic acid, formic acid, acetic acid and trifluoroacetic acid. Preferably, the acid is trifluoroacetic acid.

Suitable solvents for the hydrolysis reaction include ethers such as tetrahydrofuran, dioxane, cyclopentyl methyl ether and 1,2-dimethoxyethane; esters such as ethyl acetate and isopropyl acetate; hydrocarbons such as hexane and heptane; aromatic hydrocarbons such as toluene and xylene; halogenated aliphatic hydrocarbons such as dichloromethane and chloroform; halogenated aromatic hydrocarbons such as chlorobenzene; nitriles such as acetonitrile and propionitrile; amides such as N,N-dimethylformamide and N-methylpyrrolidone; and mixtures of any of these solvents. In particular, the solvent for the hydrolysis reaction is preferably an aromatic hydrocarbon, more preferably toluene or xylene, and most preferably toluene.

The hydrolysis reaction may be performed at a temperature between 0° C. and the boiling point of the reaction solvent. The reaction is preferably performed at a temperature of 10° C. to 110° C., and more preferably 15° C. to 40° C.

The amount of water used in the step of deprotecting the compound of formula (IV) is 0.2 to 2.0% by weight, and preferably 0.5 to 1.0% by weight with respect to the amount of the solvent. For example, when toluene is used as the solvent, the amount of water used is 0.2 to 2.0% by weight, and preferably 0.5 to 1.0% by weight with respect to the amount of toluene. By adding a small amount of water upon the reaction, an increase of the enantiomer is prevented, and the selectivity of the compound of formula (I) is increased.

Once the hydrolysis is completed, the acid is removed by washing with water, and then the product is washed with saturated saline until the PH of the water layer is 3 or more. The obtained organic layer is purified by crystallization and centrifugation, and washed with heptane, in particular n-heptane, and then dried under vacuum to obtain the compound of formula (I).

In the process according to the present invention, the compound of formula (II) is preferably prepared by an alkylation reaction comprising reacting a compound of formula (V):

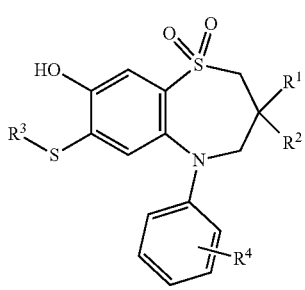

(V)

wherein $R^1$ to $R^4$ are as defined above,
with a compound of formula (VI) in the presence of water:

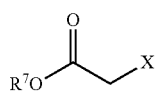

(VI)

wherein
$R^7$ is a protecting group; and
X is a leaving group;
to obtain an intermediate compound of formula (VII):

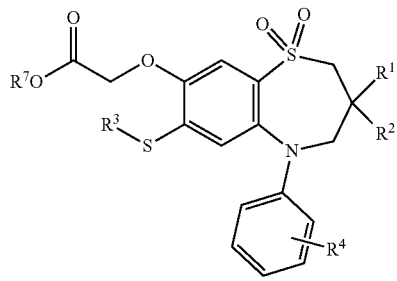

(VII)

wherein $R^1$ to $R^4$ and $R^7$ are as defined above,
followed by hydrolysis of the ester $R^7O\text{—}C(O)\text{—}$,
to obtain the compound of formula (II).

The compound of formula (VI) is an alkylating agent, and $R^7$ is preferably selected from the group consisting of $C_{1-4}$ alkyl and $C_{1-4}$ haloalkyl. More preferably, $R^7$ is $C_1$-4 alkyl such as methyl, ethyl or tert-butyl, and most preferably $R^7$ is ethyl. X is preferably selected from the group consisting of halo, trifluoromethanesulfonate, methanesulfonyl and p-toluenesulfonyl. More preferably, X is halogen, and more preferably a halogen selected from chloride, bromide and iodide. In a most preferred embodiment, the compound of formula (VI) is ethyl bromoacetate.

The compound of formula (VI) is preferably used in excess with respect to the compound of formula (V). The compound of formula (VI) is preferably used in 1.1 to 1.4 equivalents with respect to the compound of formula (V).

The step of the reaction of the compound of formula (V) with the compound of formula (VI) is performed in the presence of water. By using water as a reactant, the rate of the reaction of the compound of formula (V) with the compound of formula (VI) can be significantly increased. The amount of water used is 0.01 to 0.5% by weight, preferably 0.02 to 0.2% by weight with respect to the amount of the compound of formula (V).

The step of the reaction of the compound of formula (V) with the compound of formula (VI) is performed in the presence of a phase transfer catalyst and a base. Examples of the phase transfer catalyst include tetra-n-butylammonium bromide (TBAB), benzyltrimethylammonium chloride, benzyltriethylammonium chloride, methyltricaprylammonium chloride, methyltributylammonium chloride and methyltrioctylammonium chloride. Tetra-n-butylammonium bromide is most preferred.

Examples of the base include metal hydroxides such as sodium hydroxide, potassium hydroxide and lithium hydroxide; metal carbonates such as sodium carbonate, potassium carbonate and lithium carbonate; and metal hydrogen carbonates such as sodium hydrogen carbonate, potassium hydrogen carbonate and lithium hydrogen carbonate. The base is preferably a metal carbonate, more preferably sodium carbonate.

The base may be used in excess of the compound of formula (VI), preferably in an amount of 3.0 to 6.0 equivalents, and more preferably in an amount of 3.5 to 5.0 equivalents with respect to the compound of formula (VI).

Suitable solvents for the alkylation reaction include ethers such as tetrahydrofuran, dioxane, cyclopentyl methyl ether and 1,2-dimethoxyethane; esters such as ethyl acetate and isopropyl acetate; hydrocarbons such as hexane and heptane; aromatic hydrocarbons such as toluene and xylene; ketones such as acetone and 2-butanone; halogenated aliphatic hydrocarbons such as dichloromethane and chloroform; halogenated aromatic hydrocarbons such as chlorobenzene; nitriles such as acetonitrile and propionitrile; and amides such as N,N-dimethylformamide and N-methylpyrrolidone; and mixtures of any of these solvents. In particular, the solvent for the alkylation reaction is preferably an aromatic hydrocarbon or a halogenated aliphatic hydrocarbon, more preferably toluene or xylene, and most preferably toluene.

The alkylation reaction may be performed at a temperature between 0° C. and the boiling point of the solvent. The reaction is preferably performed at a temperature of 20° C. to 110° C., more preferably at a temperature of 50° C. to 100° C., and particularly at a temperature of 70° C. to 90° C.

Once the alkylation reaction is completed, water is added, and the phase transfer catalyst and the base are removed by extracting them to the aqueous layer. The obtained compound of formula (VII) can be used in the next step directly without further purification and isolation.

In the next step, the compound of formula (VII) is hydrolyzed, preferably under basic conditions, resulting in the compound of formula (II). The hydrolysis may be performed in an organic solvent, to which an aqueous solution of a base is added.

Examples of suitable bases include metal hydroxides such as sodium hydroxide, potassium hydroxide and lithium hydroxide; metal carbonates such as sodium carbonate, potassium carbonate and lithium carbonate; and metal hydrogen carbonates such as sodium hydrogen carbonate, potassium hydrogen carbonate and lithium hydrogen carbonate. The base is preferably a metal hydroxide, and more preferably sodium hydroxide.

The base is preferably used in excess of the compound of formula (VII). The base is preferably used in an amount of 2.0 to 6.0 equivalents, more preferably in an amount of 3.0 to 5.0 equivalents and particularly in an amount of 3.5 to 4.5 equivalents with respect to the compound of formula (VII).

Suitable solvents for the hydrolysis reaction include alcohols such as methanol, ethanol, n-propanol, isopropanol, n-butanol and t-butanol; ethers such as tetrahydrofuran, dioxane, cyclopentyl methyl ether and 1,2-dimethoxyethane; hydrocarbons such as hexane and heptane; aromatic hydrocarbons such as toluene and xylene; ketones such as acetone and 2-butanone; halogenated aliphatic hydrocarbons such as dichloromethane and chloroform; halogenated aromatic hydrocarbons such as chlorobenzene; and mixtures of any of these solvents. In particular, the solvent is preferably an alcohol or an aromatic hydrocarbon, more preferably toluene or xylene, and most preferably toluene.

It is preferable that the same solvent is used during the alkylation and the subsequent hydrolysis reaction from the perspective of the amount of solvents and the simplification of the process.

The hydrolysis is performed at a temperature between 0° C. and the boiling point of the solvent. The hydrolysis is preferably performed at a temperature of 10° C. to 110° C., more preferably at a temperature of 20° C. to 90° C., particularly at a temperature of 30° C. to 70° C.

If necessary, water and solvents are added, and then an acid such as formic acid is added to the reaction mixture. The organic layer may be cooled, and then purified by crystallization and centrifugation. The compound of formula (II) can be obtained by washing with toluene followed by drying under vacuum.

In the process according to the present invention, the compound of formula (III) is preferably prepared by deprotecting a compound of formula (VIII) in the presence of a solvent of alcohol having 3 or more carbon atoms:

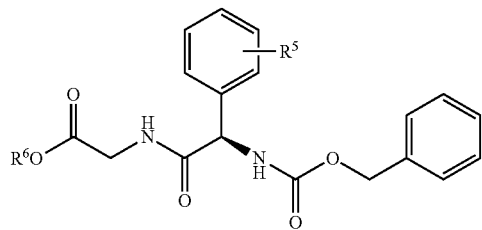

(VIII)

wherein $R^5$ and $R^6$ are as defined above.

The step of deprotecting is performed by hydrogenation of the

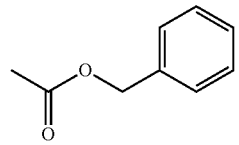

group. The step of deprotecting is performed in the presence of a suitable alcohol to obtain the compound of formula (III).

Alcohol having 3 or more carbon atoms is used as a suitable alcohol. The alcohol is preferably selected from the group consisting of 1-propanol, 2-propanol, 1-butanol, 2-butanol, 2-methyl-1-propanol, 2-methyl-2-propanol, and a mixture thereof. It is most preferable that 2-propanol is used.

The deprotecting is performed at a temperature between 0° C. and the boiling point of the alcohol used. The deprotecting is preferably performed at a temperature of 0° C. to 80° C., and more preferably at a temperature of 5° C. to 40° C.

Once the deprotecting is completed, insoluble substances are removed by filtration. The obtained residue is washed by the solvent to obtain the compound of formula (III).

The process according to the present invention can further comprise transforming the compound of formula (I) into a stable crystalline hydrate of formula (I). This may be achieved by recrystallizing the compound of formula (I) from solvents including ethanol. In a preferred embodiment, the compound of formula (I) is elobixibat and the stable crystalline hydrate of formula (I) is a crystalline monohydrate of elobixibat, most preferably crystal modification IV of elobixibat (also referred to as crystal form IV of elobixibat).

It has previously been disclosed that crystal modification IV can be obtained by crystallizing crude elobixibat from ethanol, or from a mixture of ethanol and water. A crystalline ethanolate of elobixibat is initially formed, which may be isolated and dried under vacuum at a high temperature to obtain an anhydrate of elobixibat. The anhydrate of elobixibat absorbs moisture from the air, thereby turning into crystal modification IV of elobixibat.

In the process according to the present invention, the step of transforming the compound of formula (I) into the stable crystalline hydrate of formula (I) preferably includes the step of dissolving the compound of formula (I) in ethyl acetate. In addition, the step of transforming the compound of formula (I) into the stable crystalline hydrate of formula (I) preferably includes the step of crystallizing a crystalline ethanolate of the compound of formula (I) from the solution of the compound of formula (I) in ethyl acetate.

The crystallized crystalline ethanolate of the compound of formula (I) is dried to obtain a crystalline anhydrate of the compound of formula (I). By absorbing moisture from the air, the crystalline anhydrate of the compound of formula (I) can be transformed into the stable crystalline hydrate of formula (I)

Crystal modification IV of elobixibat may have an X-ray powder diffraction (XRPD) pattern, obtained with CuKα1-radiation, with at least specific peaks at °2θ positions 6.3±0.2 and/or 19.4±0.2.

In one embodiment, crystal modification IV of elobixibat may have an X-ray powder diffraction (XRPD) pattern, obtained with CuKα1-radiation, with specific peaks at °2θ positions 6.3±0.2 and 19.4±0.2 and the characteristic peaks at one or more of °2θ positions: 10.2±0.2, 10.5±0.2, 9.4±0.2, 9.5±0.2, 12.5±0.2, 14.6±0.2, 15.6±0.2 and 23.3±0.2.

In another embodiment, crystal modification IV of elobixibat may have an X-ray powder diffraction (XRPD) pattern, obtained with CuKα1-radiation, with characteristic peaks at one or more of °2θ positions: 6.3±0.2, 19.4±0.2, 10.2±0.2, 10.5±0.2, 9.4±0.2, 9.5±0.2, 12.5±0.2, 14.6±0.2, 15.6±0.2 and 23.3±0.2, and one or more of 8.3±0.2, 11.3±0.2, 13.4±0.2, 13.9±0.2, 16.3±0.2, 16.6±0.2, 18.2±0.2, 18.8±0.2, 19.1±0.2, 19.3±0.2, 19.7±0.2, 19.8±0.2, 20.5±0.2, 21.0±0.2, 21.3±0.2, 21.4±0.2, 22.6±0.2, 22.9±0.2, 23.1±0.2, 23.9±0.2, 24.5±0.2, 24.7±0.2, 25.0±0.2, 25.2±0.2, 25.4±0.2, 25.7±0.2, 26.7±0.2, 26.9±0.2, 28.3±0.2 and 28.9±0.2.

In another embodiment, the crystal modification IV of elobixibat may have an X-ray powder diffraction (XRPD) pattern, obtained with CuKα1-radiation, with characteristic peaks at one or more of °2θ positions: 6.3±0.2, 8.3±0.2, 9.4±0.2, 9.5±0.2, 10.2±0.2, 10.5±0.2, 11.3±0.2, 12.5±0.2, 13.4±0.2, 13.9±0.2, 14.6±0.2, 15.6±0.2, 16.3±0.2, 16.6±0.2, 18.2±0.2, 18.8±0.2, 19.1±0.2, 19.3±0.2, 19.4±0.2, 19.7±0.2, 19.8±0.2, 20.5±0.2, 21.0±0.2, 21.3±0.2, 21.4±0.2, 22.6±0.2, 22.9±0.2, 23.1±0.2, 23.3±0.2, 23.9±0.2, 24.5±0.2, 24.7±0.2, 25.0±0.2, 25.2±0.2, 25.4±0.2, 25.7±0.2, 26.7±0.2, 26.9±0.2, 28.3±0.2 and 28.9±0.2.

In a preferred embodiment, the crystallization of the crystalline ethanolate of the compound of formula (I) can be initiated by the addition of a seed crystal of crystal modification IV of elobixibat.

In another preferred embodiment, n-heptane is added to the solution of the compound of formula (I) in ethyl acetate.

EXAMPLES

Although the present invention is more specifically illustrated by means of the following examples and comparative examples, the invention is not limited to the examples. Furthermore, unless otherwise stated, reagents used in the examples were purchased commercially available or prepared by methods known by a person skilled in the art.

Example 1: Preparation of 2-{[3,3-dibutyl-7-(methylsulfanyl)-1,1-dioxo-5-phenyl-2,3,4,5-tetrahydro-1H-1,5-benzothiazepin-8-yl]oxy}ethyl acetate 3,3-dibutyl-7-(methylsulfanyl)-1,1-dioxo-5-phenyl-2,3,4,5-tetrahydro-1H-1,5-benzothiazepin-8-ol (13.00 kg), sodium carbonate (12.90 kg), tetrabutylammonium bromide (0.84 kg), toluene (113.18 kg), water (0.52 kg) and ethyl bromoacetate (5.58 kg) were added in a reactor and reacted with stirring at 80° C. After the reaction was completed, the reaction solution was cooled and then washed with water to obtain 2-{[3,3-dibutyl-7-(methylsulfanyl)-1,1-dioxo-5-phenyl-2,3,4,5-tetrahydro-1H-1,5-benzothiazepin-8-yl]oxy}ethyl acetate in toluene.

Example 2: Preparation of 2-{[3,3-dibutyl-7-(methylsulfanyl)-1,1-dioxo-5-phenyl-2,3,4,5-tetrahydro-1H-1,5-benzothiazepin-8-yl]oxy}acetic acid A 10% aqueous solution of sodium hydroxide (46.49 kg) was added to the total amount of 2-{[3,3-dibutyl-7-(methylsulfanyl)-1,1-dioxo-5-phenyl-2,3,4,5-tetrahydro-1H-1,5-benzothiazepin-8-yl]oxy}ethyl acetate in toluene, which was obtained in Example 1, and reacted with stirring at 47° C. After the reaction was completed, water (77.5 kg) and toluene (124.1 kg) were added, and then formic acid (11.07 kg) was added.

The organic layer was then cooled to 5° C., and the precipitated crystal was centrifuged and washed with toluene. The crystal was dried under vacuum at 55° C. or less to obtain a dried crystal of 2-{[3,3-dibutyl-7-(methylsulfanyl)-1,1-dioxo-5-phenyl-2,3,4,5-tetrahydro-1H-1,5-benzothiazepin-8-yl]oxy}acetic acid (13.45 kg).

Example 3: Preparation of 1,1-dimethylethyl[(2R)-2-amino-2-phenylacetamide]acetate 1,1-dimethylethyl 2-[(2R)-2-benzyloxycarbamido-2-phenylacetamido]acetate (11.40 kg), 2-propanol (91.6 kg) and 10% palladium-carbon (containing 50% water) (1.37 kg) were added in a reactor. The reaction was conducted under hydrogen at a pressure of 0.03 MPa at 10° C.

Insoluble substances were removed by filtration from the reacted solution, and filtrate was washed by 2-propanol (11.4 kg) to obtain 1,1-dimethylethyl[(2R)-2-amino-2-phenylacetamide]acetate in 2-propanol.

Example 4: Preparation of 1,1-dimethylethyl[(2R)-2-(2-{[3,3-dibutyl-7-(methysulfanyl)-1,1-dioxo-5-phenyl-2,3,4,5-tetrahydro-1H-1,5-benzothiazepin-8-yl]oxy}acetamide)-2-phenylacetamide]acetate The total amount of 1,1-dimethylethyl[(2R)-2-amino-2-phenylacetamide]acetate in 2-propanol, which was obtained in Example 3, and 2-{[3,3-dibutyl-7-(methysulfanyl)-1,1-dioxo-5-phenyl-2,3,4,5-tetrahydro-1H-1,5-benzothiazepin-8-yl]oxy}acetic acid (13.20 kg), which was obtained in Example 2, were added in a reactor and stirred. 4-(4,6-dimethoxy-1,3,5-triazin-2-yl)-4-methylmopholinium chloride (DMT-MM) (10.10 kg) was added and reacted with stirring at 20° C. Insoluble substances were filtered from the obtained reaction solution, and the residue was washed by 2-propanol (26.4 kg). The filtrate was concentrated to 60.6 kg, and ethyl acetate (119.0 kg) was added to the concentrate, and the solution was washed in a sequential order with diluted hydrochloric acid, aqueous solution of sodium bicarbonate and saline. After washing, n-heptane (251.1 kg) was added to remove an aqueous layer, and seed crystals (66.00 g) of 1,1-dimethylethyl[(2R)-2-(2-{[3,3-dibutyl-7-(methysulfanyl)-1,1-dioxo-5-phenyl-2,3,4,5-tetrahydro-1H-1,5-benzothiazepin-8-yl]oxy}acetamide)-2-phenylacetamide]acetate was added to the obtained organic layer at 25° C. and stirred. After cooling to 0° C., the precipitated crystal was centrifuged and washed with n-heptane (79.2 kg) to obtain 1,1-dimethylethyl[(2R)-2-(2-{[3,3-dibutyl-7-(methysulfanyl)-1,1-dioxo-5-phenyl-2,3,4,5-tetrahydro-1H-1,5-benzothiazepin-8-yl]oxy}acetamide)-2-phenylacetamide]acetate as a wet crystal.

The obtained wet crystal was then dried under vacuum at 50° C. or less to obtain a dried crystal of 1,1-dimethylethyl[(2R)-2-(2-{[3,3-dibutyl-7-(methysulfanyl)-1,1-dioxo-5-phenyl-2,3,4,5-tetrahydro-1H-1,5-benzothiazepin-8-yl]oxy}acetamide)-2-phenylacetamide]acetate (16.87 kg).

Example 5. Preparation of [(2R)-2-(2-{[3,3-dibutyl-7-(methysulfanyl)-1,1-dioxo-5-phenyl-2,3,4,5-tetrahydro-1H-1,5-benzothiazepin-8-yl]oxy}acetamide)-2-phenylacetamide]acetic acid ethanolate 1,1-dimethylethyl[(2R)-2-(2-{[3,3-dibutyl-7-(methysulfanyl)-1,1-dioxo-5-phenyl-2,3,4,5-tetrahydro-1H-1,5-benzothiazepin-8-yl]oxy}acetamide)-2-phenylacetamide]acetate (25.00 g) which was obtained in Example 4, toluene (319.65 g), and water (1.61 g) were added in a flask, to which trifluoroacetic acid (132.73 g) was dropped, and reacted with stirring at 30° C. The reaction solution was washed in a sequential order with water (200.07 g) and 10% saline (200.06 g) and the organic layer was concentrated to 124.8 g, and then ethylacetate (200.23 g) was added. The solution was washed four times with 10% saline, and the solvent was replaced with toluene by concentration replacement, and then concentrated to 68.5 g. Ethyl acetate (37.50 g), ethanol (32.52 g), n-heptane (125.34 g) and seed crystals of elobixibat [(2R)-2-(2-{[3,3-dibutyl-7-(methylsulfanyl)-1,1-dioxo-5-phenyl-2,3,4,5-tetrahydro-1H-1,5-benzothiazepin-8-yl]oxy}acetamide)-2-phenylacetamide]acetic acid monohydrate (0.13 g) were added and stirred at 25° C., and then n-heptane (124.91 g) was added and cooled to 0° C. and further stirred. The precipitated crystal was filtered and dried under vacuum at 35° C. or less to obtain a crude crystal of elobixibat as ethanolate (21.82 g).

Example 6: Preparation of [(2R)-2-(2-{[3,3-dibutyl-7-(methylsulfanyl)-1,1-dioxo-5-phenyl-2,3,4,5-tetrahydro-1H-1,5-benzothiazepin-8-yl]oxy}acetamide)-2-phenylacetamide]acetic acid monohydrate The crude crystal of elobixibat ethanolate which was obtained in Example 5 (13.98 kg) and ethyl acetate (28.0 kg) were added in a reactor and dissolved stirring at 40° C. The obtained solution was filtered and the filtrate was washed by ethyl acetate (7.0 kg). Ethanol (25.2 kg) was then added, and seed crystals of elobixibat monohydrate (7.00 g) and n-heptane (140.2 kg) were added and stirred, and cooled to 0° C. The precipitated crystal was centrifuged and washed with n-heptane (27.9 kg). The obtained crystal was dried under vacuum at 35° C. or less to obtain elobixibat ethanolate (13.26 kg).

Purified water (124.6 kg), absolute ethanol (1.10 kg) and said elobixibat ethanolate (12.60 kg) were added in a reactor and stirred at 25° C. The obtained crystal was centrifuged and washed with purified water (41.2 kg) and dried under vacuum at 45° C. Elobixibat monohydrate (11.68 kg) was obtained by exposing nitrogen at controlled humidity and adjusting water content to 2.7%.

The process according to the present invention enable to prepare 1,5-benzothiazepine compounds in high yields and high purity, and the cost for the preparation is not expensive. In addition, the process is suitable for an industrial scale production, and thus useful.

The invention claimed is:

1. A process for the preparation of a compound of formula (I):

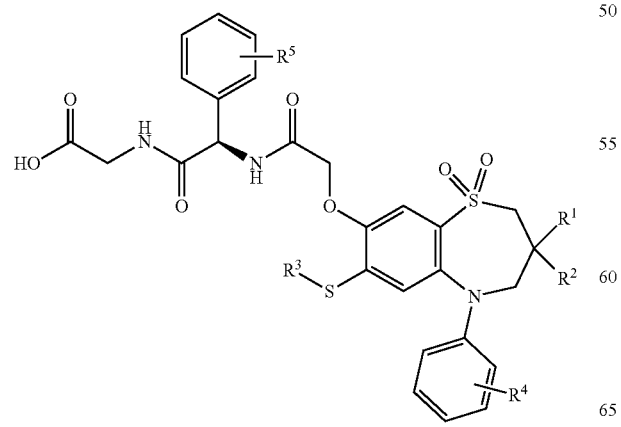

wherein
$R^1$ and $R^2$ are each independently $C_{1-4}$ alkyl;
$R^3$ is $C_{1-4}$ alkyl;
$R^4$ is selected from the group consisting of hydrogen, hydroxy, halo, nitro, cyano and $C_{1-4}$ alkyl; and
$R^5$ is selected from the group consisting of hydrogen, hydroxy, halo, nitro, cyano and $C_{1-4}$ alkyl;
comprising reacting a compound of formula (II)

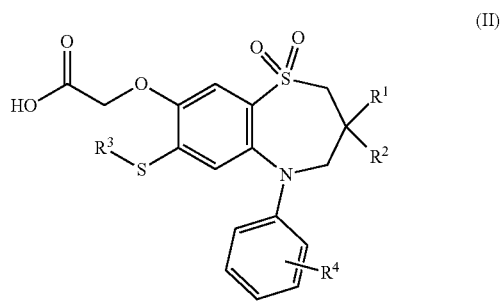

wherein $R^1$, $R^2$, $R^3$, and $R^4$ are each as defined above, with a compound of formula (III) in the presence of a triazine compound:

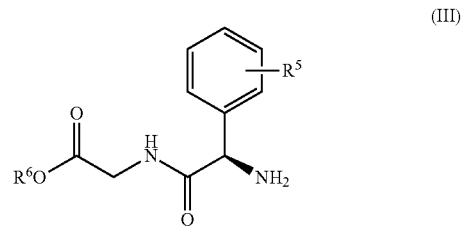

wherein
$R^5$ is as defined above; and
$R^6$ is a protecting group;
to obtain a compound of formula (IV):

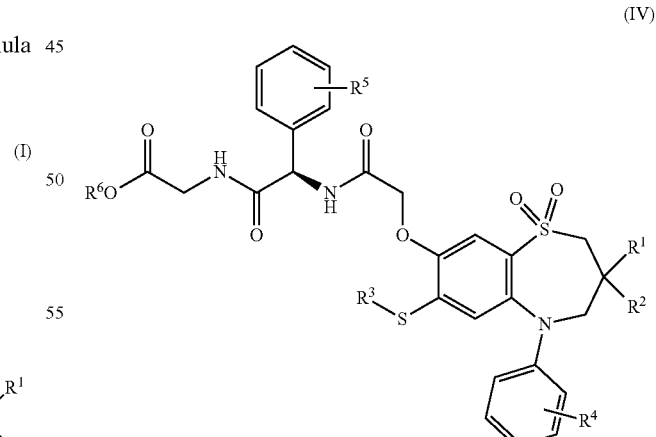

wherein $R^1$, $R^2$, $R^3$, $R^4$, $R^5$, and $R^6$ are each as defined above,
and deprotecting said compound of formula (IV) to obtain the compound of formula (I).

2. The process according to claim 1, wherein the triazine compound is selected from the group consisting of 2,4,6- trichloro-1,3,5-triazine (TCT), 2-chloro-4,6-dimethoxy-1,3,5-triazine (CDMT), 2,4-dichloro-6-methoxy-1,3,5-triazine (DCMT), 4-(4,6-dimethoxy-1,3,5-triazin-2-yl)-4-methylmorpholinium chloride (DMT-MM), and a mixture thereof.

3. The process according to claim 1, wherein $R^1$ and $R^2$ are each n-butyl.

4. The process according to claim 1, wherein $R^3$ is methyl.

5. The process according to claim 1, wherein $R^4$ and $R^5$ are each hydrogen.

6. The process according to claim 1, wherein $R^6$ is selected from the group consisting of $C_{1-4}$ alkyl and trisubstituted silyl.

7. The process according to claim 1, wherein $R^6$ is tert-butyl.

8. The process according to claim 1, wherein the compound of formula (IV) is deprotected by reacting with trifluoroacetic acid.

9. The process according to claim 1, wherein the step of deprotecting said compound of formula (IV) is performed in the presence of toluene and water, and the amount of water used is 0.2 to 2.0% by weight with respect to the amount of toluene.

10. The process according to claim 1, wherein the compound of formula (I) is precipitated from a solution by the addition of heptane.

11. The process according to claim 1, wherein the compound of formula (II) is prepared by an alkylation reaction comprising reacting a compound of formula (V):

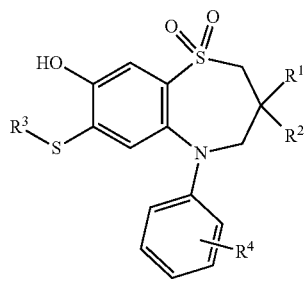

(V)

wherein
$R^1$ and $R^2$ are each independently $C_{1-4}$ alkyl;
$R^3$ is $C_{1-4}$ alkyl; and
$R^4$ is selected from the group consisting of hydrogen, hydroxy, halo, nitro, cyano and $C_{1-4}$ alkyl;
with a compound of formula (VI) in the presence of water:

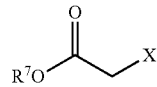

(VI)

wherein
$R^7$ is a protecting group; and
X is a leaving group;

to obtain an intermediate compound of formula (VII):

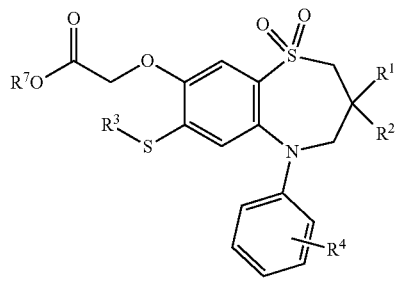

(VII)

wherein $R^1$, $R^2$, $R^3$, $R^4$, and $R^7$ are each as defined above, followed by hydrolysis of the ester $R^7O$—C(O)—, to obtain the compound of formula (II).

12. The process according to claim 11, wherein $R^7$ is selected from the group consisting of $C_{1-4}$ alkyl and $C_{1-4}$ haloalkyl.

13. The process according to claim 11, wherein X is selected from the group consisting of halo, trifluoromethanesulfonate, methanesulfonyl and p-toluenesulfonyl.

14. The process according to claim 11, wherein the preparation of the intermediate compound of formula (VII) is performed in toluene.

15. The process according to claim 11, wherein the amount of water used in the reaction of the compound of formula (V) with the compound of formula (VI) is 0.01 to 0.5% by weight with respect to the amount of the compound of formula (V).

16. The process according to claim 11, wherein the intermediate compound of formula (VII) is not isolated and used directly in the next step.

17. The process according to claim 11, wherein the alkylation reaction and the subsequent hydrolysis reaction are performed in the same solvent.

18. The process according to claim 1, wherein the compound of formula (III) is prepared by deprotecting a compound of formula (VIII) in the presence of a solvent of alcohol having 3 or more carbon atoms:

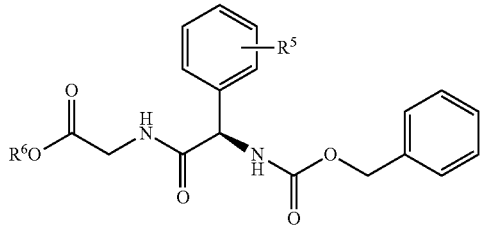

(VIII)

wherein
$R^5$ is selected from the group consisting of hydrogen, hydroxy, halo, nitro, cyano and $C_{1-4}$ alkyl; and
$R^6$ is a protecting group.

19. The process according to claim 18, wherein the alcohol having 3 or more carbon atoms is selected from the group consisting of 1-propanol, 2-propanol, 1-butanol, 2-butanol, 2-methyl-1-propanol, 2-methyl-2-propanol, and a mixture thereof.

20. The process according to claim 1, further comprising transforming the compound of formula (I) into a stable crystalline hydrate of formula (I).

21. The process according to claim 20, wherein the compound of formula (I) is dissolved in ethyl acetate.

22. The process according to claim 21, wherein n-heptane is added to the solution of the compound of formula (I) in ethyl acetate.

23. The process according to claim 20, wherein the stable crystalline hydrate is a crystalline monohydrate.

* * * * *